(12) United States Patent
Lev et al.

(10) Patent No.: US 8,531,305 B2
(45) Date of Patent: *Sep. 10, 2013

(54) METHOD OF MEASURING ELECTRICAL RESISTANCE OF JOINTS

(75) Inventors: Leonid C. Lev, West Bloomfield, MI (US); Nikolay Kondratyev, West Bloomfield, MI (US)

(73) Assignee: GM Global Technology Operations LLC, Detroit, MI (US)

( * ) Notice: Subject to any disclaimer, the term of this patent is extended or adjusted under 35 U.S.C. 154(b) by 201 days.

This patent is subject to a terminal disclaimer.

(21) Appl. No.: 13/104,112

(22) Filed: May 10, 2011

(65) Prior Publication Data

US 2012/0290228 A1    Nov. 15, 2012

(51) Int. Cl.
*G08B 21/00* (2006.01)

(52) U.S. Cl.
USPC ............... 340/635; 340/636.1; 340/636.13

(58) Field of Classification Search
USPC ...................................................... 340/635
See application file for complete search history.

(56) References Cited

U.S. PATENT DOCUMENTS

| | | | |
|---|---|---|---|
| 6,225,810 B1* | 5/2001 | Godo et al. | 324/525 |
| 2010/0045303 A1* | 2/2010 | Williams | 324/551 |
| 2011/0004429 A1* | 1/2011 | Morita et al. | 702/63 |
| 2011/0195302 A1* | 8/2011 | Bucchi et al. | 429/179 |
| 2011/0274964 A1* | 11/2011 | Tuffile | 429/156 |

* cited by examiner

*Primary Examiner* — Kerri McNally
(74) *Attorney, Agent, or Firm* — Quinn Law Group, PLLC

(57) ABSTRACT

A method for measuring electrical resistance of a joint includes supplying a first current between a first end of a first member of the joint and a first end of a second member of the joint. The method also includes measuring a first voltage between a second end of the first member and a second end of the second member. The first ends of the first member and the second member are oriented or situated opposite of the joint from the second ends of the first member and the second member. The method also includes calculating a first joint resistance of the joint from the supplied first current and the measured first voltage.

10 Claims, 4 Drawing Sheets

METHOD OF MEASURING ELECTRICAL RESISTANCE OF JOINTS

TECHNICAL FIELD

This disclosure relates generally to testing of joints and joint quality.

BACKGROUND

Many devices are assembled or manufactured with joints linking two or more components. Vehicles, and especially hybrid and hybrid-electric vehicles, include batteries for storage of electrical energy. The rechargeable battery or batteries may provide power used for vehicle traction. Furthermore, the batteries may be used to provide power for operation of accessories and for starting, lighting, and ignition functions of the vehicle.

Modern vehicles contain a large number of components. Many of these components contain several sub-component members, jointed or joined together. It is common to refer a component containing jointed members as a joined component.

SUMMARY

A method for measuring electrical resistance of a joint is provided. The method includes supplying a first current between a first end of a first member of the joint and a first end of a second member of the joint. The method includes measuring a first voltage between a second end of the first member and a second end of the second member. The first ends of the first member and the second member are situated opposite of the joint from the second ends of the first member and the second member. Therefore, the joint separates the first and second members and also defines the first and second ends. The method also includes calculating a first joint resistance of the joint from the supplied first current and the measured first voltage.

The above features and advantages and other features and advantages of the present invention are readily apparent from the following detailed description of the best modes and other embodiments for carrying out the invention when taken in connection with the accompanying drawings.

DESCRIPTION

Figure 1:
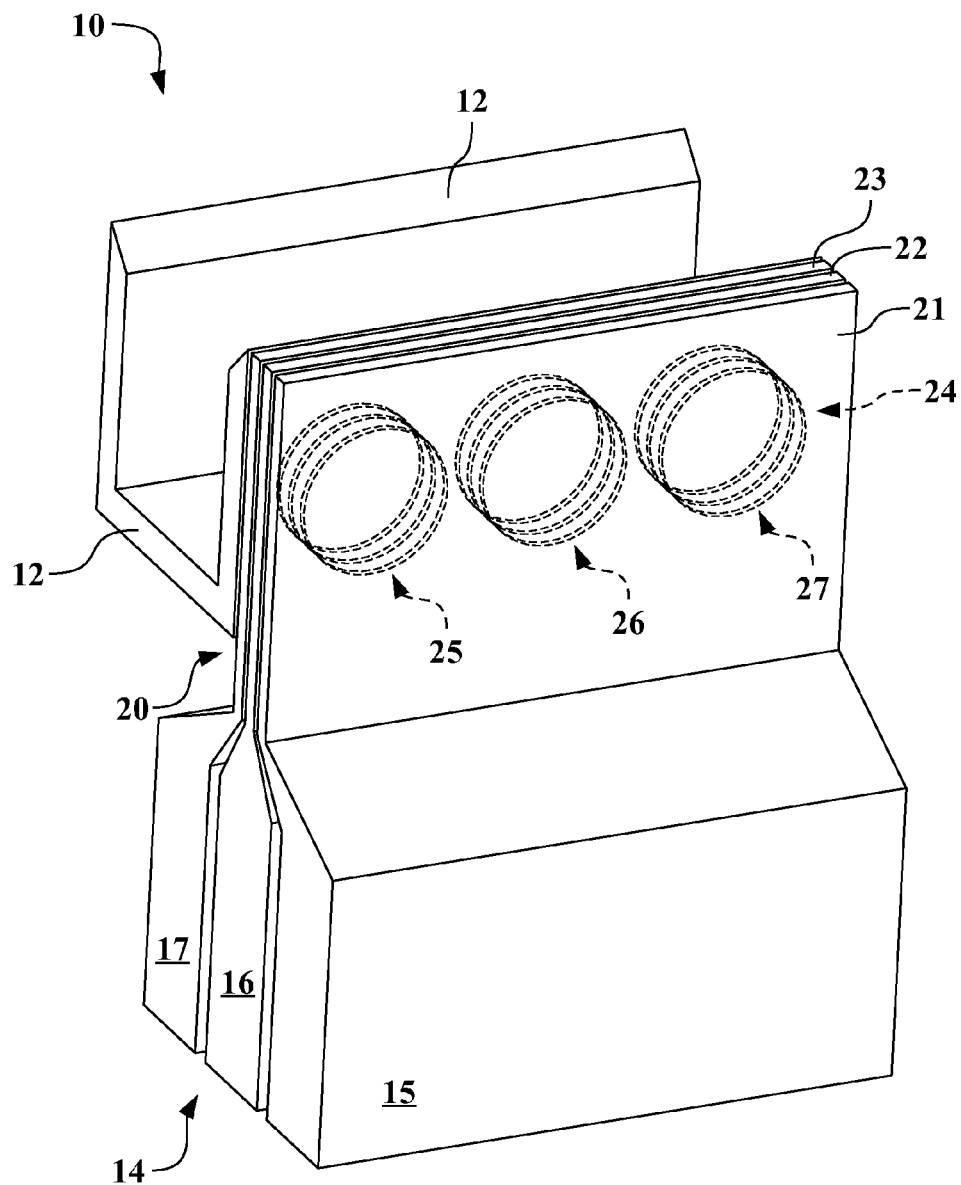
FIG. 1 is a schematic isometric view of a portion of a multi-cell battery, having a plurality of joints formed from weld nuggets.

Referring to the drawings, wherein like reference numbers correspond to like or similar components throughout the several figures, there is shown in FIG. 1 a portion of a multi-cell battery 10 for a vehicle (not shown). The battery 10 includes a plurality of joints between components. Each of the joints includes a plurality of first members or first sides, such as bus members 12 (only one of which is shown in FIG. 1) and a plurality of second members or second sides, such as battery cells 14. The first and second members are on opposing sides of the joint, and designation as first or second is not limiting. The battery cells 14 may be individually denoted as a first cell 15, a second cell 16, and a third cell 17. Features and components shown in other figures may be incorporated and used with those shown in FIG. 1.

The bus member 12 shown may be referred to as a common bus or a U-channel. The whole battery 10, or portions thereof, may alternatively be referred to as a battery pack. Furthermore, each of the first through third cells 15, 16, 17 may be configured to operate as individual batteries, which are then combined and arranged to provide specific characteristics for the battery 10, as required by the specific hybrid or hybrid-electric vehicles into which the battery 10 may be incorporated. As described herein, the attachments for only one side of the bus member 12 are fully shown, and each side of the bus member 12 may be in communication with fewer or more battery cells 14 than shown. The exact configurations of the portion of the battery 10 shown in the figures are illustrative only and do not limit the scope of the invention.

The battery cells 14 are attached to the bus member 12 through a plurality of tabs 20, which are on the second members of the joints. The first, second, and third cells 15, 16, and 17, include a first tab 21, a second tab 22, and a third tab 23, respectively. Each of the battery cells 14 and tabs 20 may be substantially identical, such that any individual battery cell 14 may be designated as first, second, or third.

Electrical connection between the bus member 12 and the tabs 20 occurs through a plurality of weld joints 24. The weld joints 24 are composite joints formed from the individual weld nugget joints. Specific weld joints 24 may be referred to as a first weld stack 25, a second weld stack 26, and a third weld stack 27. More or fewer weld joints 24 may be used to electrically connect the tabs 20 to the bus member 12.

Figure 2A:
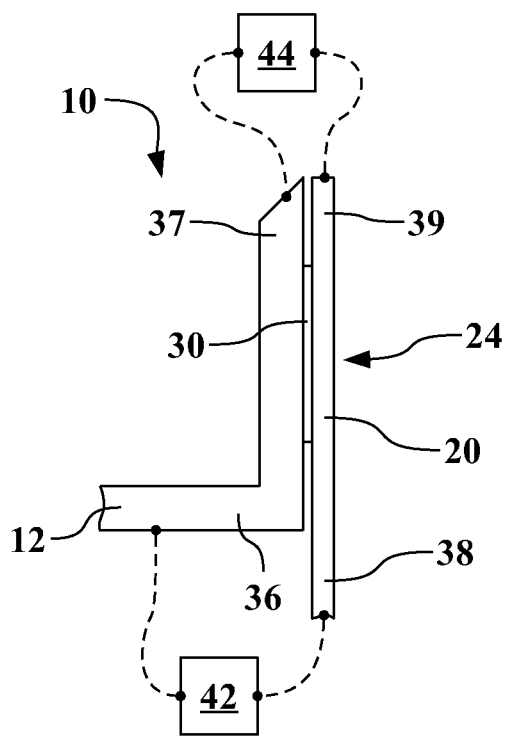
FIG. 2A is a schematic side view of a portion of a battery cell similar to that shown in FIG. 1, but having a single-tab configuration.
Figure 2B:
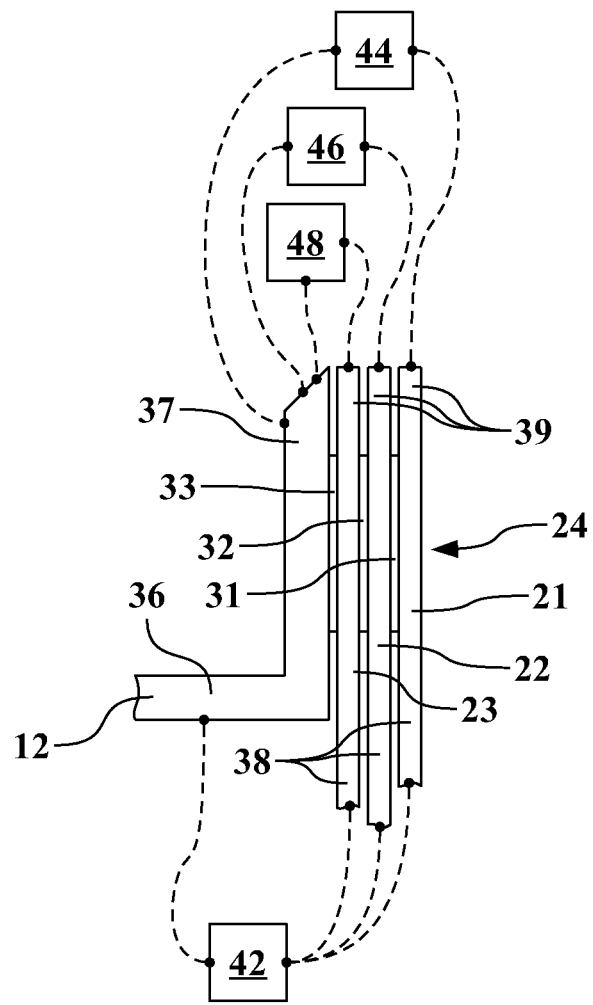
FIG. 2B is a schematic side view of a portion of a battery cell similar to that shown in FIG. 1, and having a three-tab configuration.

Referring now to FIG. 2A and FIG. 2B, and with continued reference to FIG. 1, there are shown two side views of portions of batteries 10 similar to the portion of the battery 10 shown in FIG. 1. FIG. 2A shows a side view of a single-tab configuration in which the tab 20 is welded directly to the bus member 12, such that the weld joint 24 has only one weld nugget 30. FIG. 2B shows a side view of a three-tab configuration in which three tabs 20 are all welded to the bus member 12, such that the weld joint 24 has three weld nuggets 30, a first weld nugget 31, a second weld nugget 32, and a third weld nugget 33. Features and components shown in other figures may be incorporated and used with those shown in FIGS. 2A and 2B.

Although illustrated as separately-identifiable components, the weld nuggets 30 may generally be considered as zones of coalescence between the adjacent tabs 20. Furthermore, adjacent tabs 20 may be pressed together during assembly, such that a side-view would not necessarily show the individual weld nuggets 30 between the tabs 20. The weld nuggets 30 may be of varying thickness and area and may be formed by resistance welding, ultrasonic welding, or other suitable welding processes. The weld nuggets 30, individually, or the weld joints 24 may also be referred to as joints or weld joints. The weld nuggets 30 may be individually measured or checked for joint integrity or the weld joints 24 may be measured for overall joint integrity.

As shown in FIG. 2A, the bus member 12 has a first end 36 and a second end 37, which are disposed on opposing sides of the weld nugget 30. Similarly, the tab 20 has a first end 38 and a second end 39, which are also disposed on opposing sides of the weld nugget 30. The first end 36 of the bus member 12 and the first end 38 of the tab 20 are on the same relative side of the weld nugget 30. The location of the weld nugget 30, or the other joint types, defines the relative location of the first ends 36, 38 and the second ends 37, 39. Therefore, the first ends 36, 38 are below (as viewed in the figures) the joint and the second ends 37, 39 are above (as viewed in the figures) the joint.

The battery cell 14 (not shown in FIG. 2A) or the tab 20 is connected to a current source 42, which supplies a current between the first end 36 of the bus member 12 and the first end 38 of the tab 20 via wires or conductors (shown as dashed lines). In order to move between the first end 36 of the bus member 12 and the first end 38 of the tab 20, the current moves through the weld nugget 30. The current source 42 may include a voltage source and a precision resistor. Therefore, the current source 42 may also supply a voltage at a controlled resistance between the first end 36 of the bus member 12 and the first end 38 of the tab 20. A first voltmeter 44 measures a voltage differential between the second end 37 of the bus member 12 and the second end 39 of the tab 20.

From the current and the measured voltage, it is possible to calculate the resistance of the weld nugget 30. The calculated resistance may be indicative of the quality of the weld nugget 30. For example, if the weld nugget 30 does not include continuous coalescence between the tab 20 and the bus member 12, flow of the current from the tab 20 to the bus member 12 may be impeded, causing the calculated resistance to increase. Furthermore, if the weld nugget 30 is broken or has significant cracking, the calculated resistance may also increase greatly.

The three-tab configuration shown in FIG. 2B may be the same configuration of the battery 10 as is shown in FIG. 1. The weld joint 24 shown in FIG. 2B includes the first weld nugget 31, the second weld nugget 32, and the third weld nugget 33. The weld joint 24 may be any of the first weld stack 25, the second weld stack 26, and the third weld stack 27 shown in FIG. 1.

The first tab 21 has a first end 38 and a second end 39, which are disposed on opposing sides of the first weld nugget 31. The first end 36 of the bus member 12 and the first end 38 of the first tab 21 are on the same relative side of the first weld nugget 31. Similarly, the second tab 22 has a first end 38 and a second end 39 disposed on opposing sides of the second weld nugget 32, and the third tab 23 has a first end 38 and a second end 39 disposed on opposing sides of the third weld nugget 33.

The current supply 42 is connected to the first ends 38 of the first tab 21, the second tab 22, and the third tab 23. A first current ($I_1$) is supplied by the current supply 42 between the first end 36 of the bus member 12 and the first end 38 of the first tab 21. Similarly, a second current ($I_2$) is supplied by the current supply 42 between the first end 36 of the bus member 12 and the first end 38 of the second tab 22, and a third current ($I_3$) is supplied by the current supply 42 between the first end 36 of the bus member 12 and the first end 38 of the third tab 23. The first current, the second current, and the third current may be substantially equal, such that each is approximately one-third of a total stack current (I) supplied by the current supply 42.

$$I_1 = I_2 = I_3 = I/3$$

The first voltmeter 44 measures a first voltage ($V_1$) between the second end 37 of the bus member 12 and the second end 39 of the first tab 21. A second voltmeter 46 is attached to the second end 37 of the bus member 12 and the second end 39 of the second tab 22, and measures a second voltage ($V_2$) therebetween. A third voltmeter 48 is attached to the second end 37 of the bus member 12 and the second end 39 of the third tab 23, and measures a third voltage ($V_3$) therebetween.

Electrical current in metallic conductors is realized through flow of electrons. Ohm's law states that the current through a conductor between two points is directly proportional to the potential difference across the two points. The coefficient of proportionality is an inverse of the resistance between the two points.

The current in metallic conductors usually obeys Ohm's law. Therefore, the ratio of the voltage to current applied to a metallic conductor or set of conductors, caused by this voltage, is constant and may be called the effective resistance of the set of conductors to the voltage or current applied.

From the total stack current and from the measured first, second, and third voltages, the resistance of each of the first, second, and third weld nuggets 31, 32, 33 may be calculated. A first nugget resistance ($R_{12}$) is the resistance of only the first weld nugget 31 between the first tab 21 and the second tab 22. A second nugget resistance ($R_{23}$) is the resistance of only the second weld nugget 32 between the second tab 22 and the third tab 23. A third nugget resistance ($R_{3b}$) is the resistance of only the third weld nugget 33 between the third tab 23 and the bus member 12. The first, second, and third nugget resistances can be determined or calculated as three unknowns in three equations.

$$V_1 = I^* (1/3 * R_{12} + 2/3 * R_{23} + R_{3b})$$

$$V_2 = I^* (2/3 * R_{23} + R_{3b})$$

$$V_3 = I^* (R_{3b})$$

The individual resistances of each of the first weld nugget 31, the second weld nugget 32, and the third weld nugget 33 may be compared to weld quality range having a predetermined minimum nugget resistance and a predetermined maximum nugget resistance. The results of the comparison may then be output to a receiver, which may be, for example and without limitation: a computer logging data, an operator testing the battery 10 or portions thereof, or an automated testing and sorting process. The specific values of the weld quality range may vary greatly based upon the type of battery 10, the materials used for the tabs 20, and the type of welding process used to create the weld nuggets 30 and the weld joints 24.

The results of the comparisons may include, for example and without limitation: a measurement error, a failed joint, and an acceptable joint. When the measured joint is a welded joint, the results of the comparisons may include, for example and without limitation: a measurement error, a failed weld, and an acceptable weld. The measurement error result may be output if the calculated first resistance is below the predetermined minimum nugget resistance. While low resistance generally indicates a better-quality weld, it may be assumed that below the predetermined minimum resistance there is a testing error because even welds of the best quality cannot reduce resistance below, for example, the resistance of the solid materials used.

The failed weld result may be output if the calculated first resistance is above the predetermined maximum nugget resistance, indicating that the weld quality is low and current is having difficulty flowing through the weld joint 24. The acceptable weld result may be output if the calculated first resistance is above the predetermined minimum nugget resistance and below the predetermined maximum nugget resistance such that the resistance falls within the weld quality range.

Comparison of the individual resistances may reveal problems in manufacturing or assembly of the battery 10. For example, and without limitation, after several tests and comparisons, it may be determined that the third weld nugget 33 is often not fully-formed, and the welding process may be adjusted accordingly.

In addition to solving the three equations for the resistance of each of the individual nuggets, the parenthetical quantities may be determined as resistance constants for portions of the weld joint 24. A first weld stack resistance (R1) is the total resistance of the weld joint 24, and may be indicative of the total quality of the weld joint 24 as a whole. The resistance constant for the weld joint 24 is not the resistance of any specific element, but is the total effective resistance between the first tab 21 and the bus member 12.

$$V_1 = I^*(R_1)$$

A weld quality range may also be applied to the resistance constant for the whole weld joint 24, such that the first weld stack resistance is compared to a predetermined minimum stack resistance and a predetermined maximum stack resistance. The individual resistances of the first, second, and third weld nuggets 31, 32, 33 may help identify specific manufacturing flaws. The resistance constant for the whole weld joint 24, however, may help identify successful assembly of that portion of the battery 10 for quality control. It may be that each of the weld joints 24 needs to function for the battery 10 to clear inspection. In such a case, it may be irrelevant which of the weld nuggets 30 within the weld joint 24 has defaults.

The weld joint 24 may be the first weld stack 25 shown in FIG. 1. Similarly, referring to FIG. 1, each of the first weld stack 25, the second weld stack 26, and the third weld stack 27 may have the total current supplied between the first end 38 of the first tab 21 and the first end 36 of the bus member 12. One voltmeter may be connected above each of the first through third weld stacks 25-27 (similar to the first voltmeter 44 shown in FIG. 2B) to the second end 39 of the first tab 21 and the second end 37 of the bus member 12.

From the total current supplied below each of the first through third weld stacks 25-27 and from the voltage measured above each of the first through third weld stacks 25-27, the resistance constant may be determined for each of the first through third weld stacks 25-27. Furthermore, the resistance constants of each of the first through third weld stacks 25-27 may be compared to the weld quality range to determine whether the total stack weld quality is within the predetermined range. Because the first through third weld stacks 25-27 represent easier paths for current flow than directly between the un-welded portions of the tabs 20, the tabs 20 may be treated as if they are electrically separate (or have air gaps) between the first through third weld stacks 25-27 when determining the resistance thereof.

Figure 3:
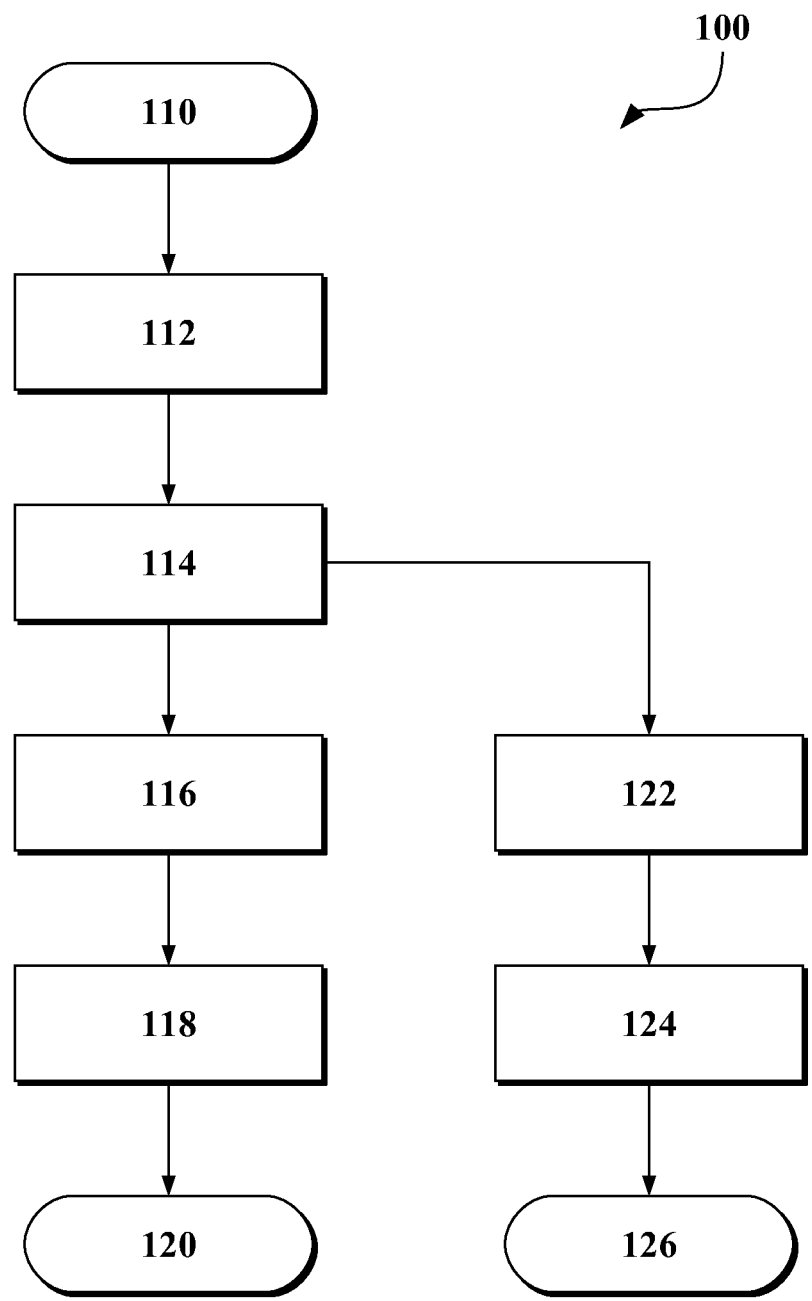
FIG. 3 shows a schematic flow chart diagram of an algorithm or method for testing the resistance of welds in a multi-cell battery, such as that shown in FIG. 1.

Referring now to FIG. 3 there is shown a schematic flow chart diagram of an algorithm or method 100 for non-destructive testing and measurement of joined components, such as the multi-cell battery 10 shown in FIG. 1. The exact order of the steps of the algorithm or method 100 shown in FIG. 3 is not required. Steps may be reordered, steps may be omitted, and additional steps may be included. Furthermore, the method 100 may be a portion or sub-routine of another algorithm or method. FIG. 3 shows only a high-level diagram of the method 100.

For illustrative purposes, the method 100 may be described with reference to some of the elements and components shown and described in relation to FIG. 1. However, other components may be used to practice the method 100 and the invention defined in the appended claims. Any of the steps may be executed by multiple components within a control system.

Step 110: Start.

The method 100 may begin at a start or initialization step, during which time the method 100 is monitoring operating conditions of the joined component or the testing equipment upon which the joined component is mounted. Initiation may occur in response to a signal from an operator.

Step 112: Supply Individual Currents.

The method 100 includes supplying a first current between a first end of a first member, such as the bus member 12, and the first end of a second member, such as the first tab 20. If the joined component has a single-tab configuration, the first current may be the only current supplied. However, for multi-component or multi-tab configurations, the method 100 also includes supplying the second current between the first end of the first member and the first end of the second tab, and supplying the third current between the first end of the first member and the first end of the third tab. The first current, the second current, and the third current may be substantially equal, such that each is one-third of the total stack current.

Step 114: Measure Individual Voltages.

The method 100 includes measuring the first voltage between the second end of the first member and the second end of the second member. The first ends of the first member and the second member are oriented opposite of the first joint from the second ends of the first member and the second member, and the first ends of the second tab and the third tab are similarly-oriented. The method 100 may also include measuring the second voltage between the second end of the first member and the second end of the second tab, and measuring the third voltage between the second end of the first member and the second end of the third tab.

Step 116: Calculate Individual Joint Resistances.

The method 100 includes calculating a first joint resistance of the first joint from the supplied first current and the measured first voltage. Depending upon the configuration of the joined component, this may be determined directly or may need to be determined in conjunction with calculating the second joint resistance of the second joint from the supplied second current and the measured second voltage and with calculating the third joint resistance of the third joint from the supplied third current and the measured third voltage. The three individual resistances of the first, second, and third joints may be determined by solving three equations for the three unknowns.

If measuring only a single weld nugget (i.e., a single weld joint), the joint resistance may simply be a measured resistance in ohms. However, when multiple components have multiple individual welds within the whole joint, such as with the weld joint 24, the ratio of voltage to current provides the resistance constant of the whole joint. The resistance constant may also be referred to as the effective resistance, and is the ratio of the first voltage to the total stack current. As used herein, "joint resistance" may refer to actual resistance of a single joint between two components or may refer to the effective resistance of multiple joints between multiple components, as measured by the ratio of voltage to current.

Step 118: Compare Individual Ranges.

The method 100 includes comparing the calculated first resistance to the predetermined minimum joint resistance and to the predetermined maximum joint resistance. The predetermined maximum joint resistance is greater than the predetermined minimum joint resistance. The second resistance and the third resistance may also be compared to the predetermined minimum joint resistance and to the predetermined maximum joint resistance.

Step 120: Output Joint Results; End.

The method 100 includes outputting the result of the comparison to the receiver. As discussed above, the results may include: measurement error, if the calculated first resistance is below the predetermined minimum joint resistance; failed joint, if the calculated first resistance is above the predetermined maximum joint resistance; and acceptable joint, if the calculated first resistance is above the predetermined minimum joint resistance and below the predetermined maximum joint resistance.

The method 100 may end after outputting the results of the comparison with the joint quality range. The end step may actually be a return to start, or the method 100 may wait until called upon again.

Step 122: Calculate Stack Resistance.

When applied to a joined component having a multi-tab configuration with multiple, stacked joints, such as the multi-cell battery 10, the method 100 may include calculating a weld stack resistance from the supplied total stack current and the measured first voltage. The stack resistance may be calculated for the first weld stack, the second weld stack, and the third weld stack. The weld stacks may be referred to as composite joints.

Step 124: Compare Stack Range.

The method may include comparing the calculated first weld stack resistance to the predetermined minimum stack resistance and to the predetermined maximum stack resistance. The predetermined maximum stack resistance is greater than the predetermined minimum stack resistance.

Step 126: Output Stack Results; End.

The method 100 includes outputting the result of the comparison of the weld stack resistance and the weld quality range to the receiver. The results may include: measurement error, failed weld, and acceptable weld. The measurement error results if the calculated first weld stack resistance is below the predetermined minimum stack resistance. The failed weld results if the calculated first weld stack resistance is above the predetermined maximum stack resistance. The acceptable weld results if the calculated first weld stack resistance is above the predetermined minimum stack resistance and below the predetermined maximum stack resistance.

Figure 4A:
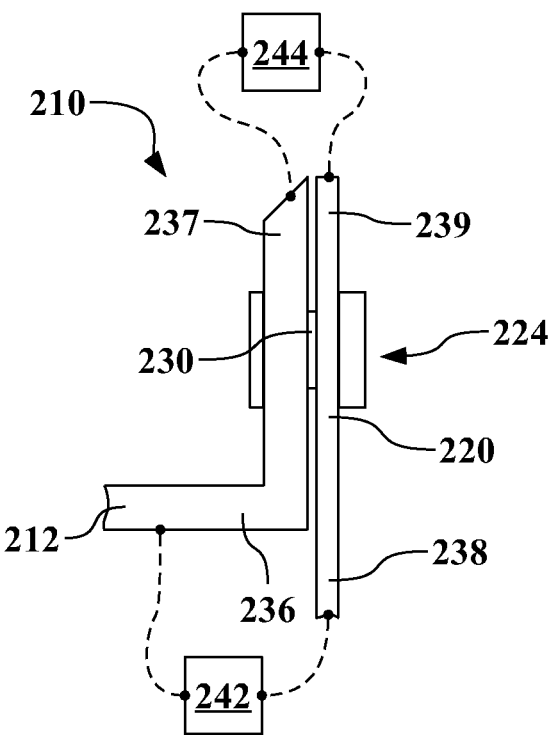
FIG. 4A is a schematic side view of a portion of a mechanical joint formed by a bolt or rivet.
Figure 4B:
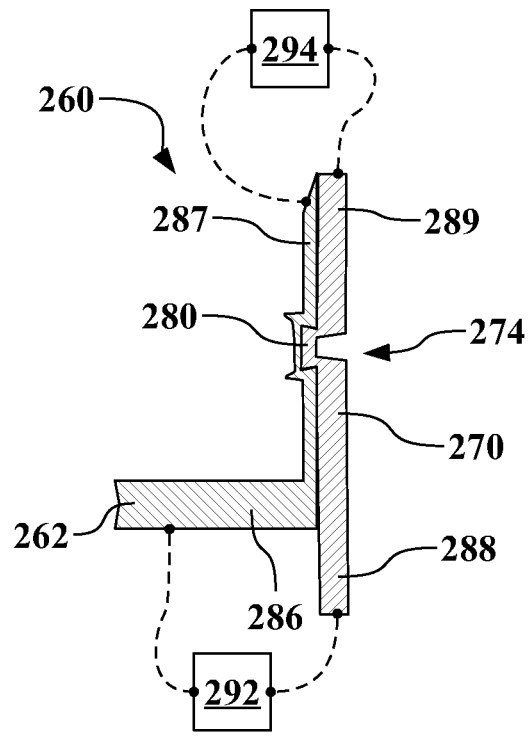
FIG. 4B is a schematic side view of a portion of a mechanical joint, formed by a clinch.

Referring now to FIG. 4A and FIG. 4B, and with continued reference to FIGS. 1-3, there are shown two views of components linked by joints. FIG. 4A shows a side view of a joined component 210 formed by a fastener. FIG. 4B shows a cross-sectional view of a joined component 260 formed by deformation. FIGS. 4A and 4B illustrate additional joint types which may be used with the methods or processes described herein. Features and components shown in other figures may be incorporated and used with those shown in FIGS. 4A and 4B.

FIG. 4A shows the joined component having a first member 212 and a second member 220. The first and second members 212 and 220 are defined on opposing sides of a mechanical joint 224. Unlike the joints shown in FIGS. 1, 2A, and 2B, the mechanical joint 224 joins the first member 212 and the second member 220 with a mechanical fastener 230, which may be, for example and without limitation: a bolt or a rivet. As used herein, mechanical joint refers to joints in which no welding and no metallurgical bond has been formed.

The first member 212 has a first end 236 and a second end 237 disposed on opposite sides of the first member 212 from the mechanical joint 224. A first end 238 and a second end 239 disposed on opposite sides of the second member 220 from the mechanical joint 224.

The quality or strength of the mechanical joint 224 may be correlated with its resistance. In order to measure the resistance of the mechanical joint 224, a current source 242 is in electrical communication with the first end 236 of the first member 212 and the first end 238 of the second member 220. The current source 242 passes a known (or measurable) electrical current through the mechanical joint 224. The current source 242 may include a voltage source and a precision resistor.

A voltmeter 244 measures a voltage differential between the second end 237 of the first member 212 and the second end 239 of the second member 220. From the supplied current and the measured voltage, it is possible to calculate the resistance of the mechanical joint 224. The calculated resistance may be indicative of the quality of the mechanical joint 224 formed by the mechanical fastener 230.

For example, if the mechanical joint 224 does not provide sufficient contact between second member 220 and the first member 212, flow of the current from the second member 220 to the first member 212 may be impeded, causing the calculated resistance to increase. Furthermore, if the mechanical fastener 230 is broken or has significant cracking, the calculated resistance may also increase greatly.

FIG. 4B shows the joined component having a first member 262 and a second member 270. The first and second members 262 and 270 are defined on opposing sides of a mechanical joint 274. Unlike the joints shown in FIGS. 1, 2A, and 2B, the mechanical joint 274 joins the first member 262 and the second member 270 with a clinching region 280. Alternatively, the clinching region 280 may be replaced with, for example and without limitation, a hemmed region or other mechanical joints.

The first member 262 has a first end 286 and a second end 287 disposed on opposite sides of the first member 262 from the mechanical joint 274. A first end 288 and a second end 289 disposed on opposite sides of the second member 270 from the mechanical joint 274.

The quality or strength of the mechanical joint 274 may be correlated with its resistance. In order to measure the resistance of the mechanical joint 274, a current source 292 is in electrical communication with the first end 286 of the first member 262 and the first end 288 of the second member 270. The current source 292 passes a known (or measurable) electrical current through the mechanical joint 274. The current source 292 may include a voltage source and a precision resistor.

A voltmeter 294 measures a voltage differential between the second end 287 of the first member 262 and the second end 289 of the second member 270. From the supplied current and the measured voltage, it is possible to calculate the resistance of the mechanical joint 274 and the clinching region 280. The calculated resistance may be indicative of the quality of the mechanical joint 274 formed by the clinching region 280.

For example, if the clinching region 280 does not provide sufficient contact between the second member 270 and the first member 262, flow of the current from the second member 270 to the first member 262 may be impeded, causing the calculated resistance to increase. Furthermore, if the clinching region 280 is broken, has significant cracking, or significant separation or gaps, the calculated resistance may also increase greatly.

While the present invention may be described in detail with respect to automotive applications, those skilled in the art will recognize the broader applicability of the invention. Those having ordinary skill in the art will recognize that terms such as "above," "below," "upward," "downward," et cetera, are used descriptively of the figures, and do not represent limitations on the scope of the invention, as defined by the appended claims.

While the best modes and other modes for carrying out the claimed invention have been described in detail, those familiar with the art to which this invention relates will recognize various alternative designs and embodiments for practicing the invention within the scope of the appended claims.

The invention claimed is:

1. A method for measuring electrical resistance of a joint, comprising:
   supplying a first electrical current between a first end of a first member of the joint and a first end of a second member of the joint;
   measuring a first electrical voltage between a second end of the first member and a second end of the second member;
   wherein the first end and the second end of the first member are situated on opposing sides of the joint, and the first end and the second end of the second member are situated on opposing sides of the joint
   calculating a first joint resistance of the joint from the supplied first current and the measured first voltage;
   comparing the calculated first joint resistance to a predetermined minimum joint resistance;
   comparing the calculated first joint resistance to a predetermined maximum joint resistance, wherein the predetermined maximum joint resistance is greater than the predetermined minimum joint resistance; and
   outputting a result of the comparison to a receiver, wherein the result includes:
      a measurement error, if the calculated first joint resistance is below the predetermined minimum joint resistance,
      a failed joint, if the calculated first joint resistance is above the predetermined maximum joint resistance, and
      an acceptable joint, if the calculated first joint resistance is above the predetermined minimum joint resistance and below the predetermined maximum joint resistance.

2. The method of claim 1, wherein the joint has a first weld nugget and the calculated first joint resistance is the resistance of the first weld nugget.

3. The method of claim 2, wherein the first member is a bus member and the second member is a first tab of a battery, and further comprising:
   supplying a second current between the first end of the bus member and a first end of a second tab, wherein the second tab is opposite the bus member from a second weld nugget;
   measuring a second voltage between the second end of the bus member and a second end of the second tab, wherein the first ends of the bus member and the second tab are oriented opposite of the second weld nugget from the second ends of the bus member and the second tab;
   calculating a second nugget resistance of the second weld nugget from the supplied second current and the measured second voltage;
   supplying a third current between the first end of the bus member and a first end of a third tab, wherein the third tab is opposite the bus member from a third weld nugget;
   measuring a third voltage between the second end of the bus member and a second end of the third tab, wherein the first ends of the bus member and the third tab are oriented opposite of the third weld nugget from the second ends of the bus member and the third tab;
   calculating a third nugget resistance of the third weld nugget from the supplied third current and the measured third voltage; and
   wherein the second nugget is disposed between the first nugget and the bus member and wherein the third nugget is disposed between the second nugget and the bus member, such that the first nugget, second nugget, and third nugget form a first weld stack.

4. The method of claim 3, wherein the first current, the second current, and the third current are substantially equal.

5. The method of claim 4, further comprising:
   supplying the first current, the second current, and the third current from a total stack current, such that the sum of the first current, the second current, and the third current is equal to the total stack current;
   calculating a first weld stack resistance from the supplied total stack current and the measured first voltage, wherein the first weld stack resistance is the effective resistance of the first through third tabs, the first through third weld nuggets, and the bus member.

6. The method of claim 5, further comprising:
   comparing the calculated first weld stack resistance to a predetermined minimum stack resistance;
   comparing the calculated first weld stack resistance to a predetermined maximum stack resistance, wherein the predetermined maximum stack resistance is greater than the predetermined minimum stack resistance; and
   outputting a result of the comparison to the receiver, wherein the result includes:
      a measurement error, if the calculated first weld stack resistance is below the predetermined minimum stack resistance,
      a failed weld, if the calculated first weld stack resistance is above the predetermined maximum stack resistance, and
      an acceptable weld, if the calculated first weld stack resistance is above the predetermined minimum stack resistance and below the predetermined maximum stack resistance.

7. The method of claim 6, wherein calculating the first weld stack resistance includes dividing the measured first voltage by the supplied total stack current.

8. The method of claim 7, wherein the total stack current is generated during charging of a battery cell.

9. The method of claim 1, wherein the joint is a mechanical joint.

10. The method of claim 9, wherein the mechanical joint is one of a bolt, a rivet, a clinch, and a hem, and wherein the first joint resistance is the resistance of the mechanical joint.

* * * * *